United States Patent [19]
Bidart et al.

[11] Patent Number: 5,496,551
[45] Date of Patent: Mar. 5, 1996

[54] PEPTIDE STRUCTURES, IMMUNOGENS CONTAINING THEM AND THEIR USES IN THE CONTROL OF FERTILITY

[75] Inventors: Jean-Michel Bidart, Paris; Dominique Bellet, Puteaux; Claude Bohuon, Paris, all of France

[73] Assignee: Lafon Pharma S.A., Fribourg, France

[21] Appl. No.: 34,621

[22] Filed: Mar. 19, 1993

Related U.S. Application Data

[63] Continuation of Ser. No. 827,867, Jan. 30, 1992, abandoned, which is a continuation of Ser. No. 270,975, Nov. 14, 1988, abandoned.

[30] Foreign Application Priority Data

Nov. 26, 1987 [FR] France .................................. 87 16420

[51] Int. Cl.⁶ .......................... A61K 39/38; A61K 35/22; C07K 14/59; C07K 19/00
[52] U.S. Cl. .................... 424/185.1; 424/184.1; 424/194.1; 424/195.11; 424/546; 530/397; 530/326; 530/403; 530/405
[58] Field of Search .................... 424/88, 184.1, 424/546, 185.1, 195.11; 530/397, 326, 398, 403, 405, 406; 514/8, 2

[56] References Cited

U.S. PATENT DOCUMENTS

| | | | |
|---|---|---|---|
| 4,201,770 | 5/1980 | Stevens | 424/88 |
| 4,384,995 | 5/1983 | Stevens | 424/88 |
| 4,517,290 | 5/1985 | Iwasa et al. | 424/88 |
| 4,639,512 | 1/1987 | Audibert et al. | 424/88 |
| 4,746,508 | 5/1988 | Carey et al. | 424/88 |
| 4,780,312 | 10/1988 | Talwar | 424/88 |
| 4,904,584 | 2/1990 | Shaw | 435/69.4 |

OTHER PUBLICATIONS

Aitkin, R. J. et al., "Contraceptive vaccines", Brit. Med. Bull. 49(1):88–99 (1993).
Sunhofer, S. et al. FASEB J. 7:1381–1385 (1993).
Charlesworth, M. et al., *J. Biol. Chem.*, 262(28): 13409–13416, 1987.
J.–M. Bidart et al., "Immunochemical mapping of a specific domain on human choriogonadotropin using anti–protein and anti–peptide monoclonal antibodies", The Journal of Biological Chemistry, vol. 262, No. 32, 1987, pp. 15483–15489.
V. C. Stevens, "Current status of antifertility vaccines using gonadotropin immunogens", Immunology Today, vol. 7, 1986, pp. 369–374.
B. B. Saxena, "Chemical synthesis of peptide fragments of the hormone–specific beta–subunit of human follicle–stimulating hormone", Biochemistry, vol. 24, No. 3, 1985, pp. 813–816.

*Primary Examiner*—Mary E. Mosher
*Assistant Examiner*—Laurie Scheiner
*Attorney, Agent, or Firm*—Jacobson, Price, Holman & Stern

[57] ABSTRACT

The subject of the present invention is a peptide structure comprising at least the sequence 106–116 of a β-CG or a β-LH a sequence of at least 5 amino acids containing at least one lysine residue.

These structures may be used for the preparation of vaccines intended to control fertility.

12 Claims, No Drawings

PEPTIDE STRUCTURES, IMMUNOGENS CONTAINING THEM AND THEIR USES IN THE CONTROL OF FERTILITY

This application is a continuation of U.S. application Ser. No. 07/827,867 filed Jan. 30, 1992, now abandoned, which is a continuation of U.S. Ser. No. 07/270,975, filed Nov. 14, 1988, abandoned.

The present invention relates to peptide structures and synthetic immunogens containing these peptide structures and their uses, in particular, as vaccines in a process for the control of fertility in humans and animals.

The present invention relates in particular to anti-hCG vaccines and anti-LH vaccines.

The human chorionic gonadotropin (hCG) is one of the glycoprotein hormones. Four of these hormones exhibit closely related structures; in addition to hCG, they are the luteinizing hormone (hLH), follicle stimulating hormone (hFSH) and thyrotropin (hTSH) and each comprises $\alpha$ and $\beta$ subunite linked together by noncovalent bonds. The $\alpha$ subunit is identical in the four hormones and the structures of the $\beta$ subunits exhibit a considerable degree of homology. In particular, 82% of the residues of $\beta$-hCG and $\beta$-hLH are similar and $\beta$-hCG differs from $\beta$-hLH essentially with respect to the 30 residues of the carboxyl terminal portion.

This homology between the sequences also exists in other species and regions which have been highly conserved in the course of evolution are detectable not only among different species for one and the same hormone (LH) but also between the hormones (CG/LH).

Furthermore, it will be recalled that the CG hormones only exist in the most highly evolved mammals and that in other animals the function of the CG hormones is fulfilled by the LH hormones.

It is known that hCG has an important role in the establishment and the development of pregnancy, while the biological role of hCG is still not completely known it seems that its principal role is that of being the signal sent by the fertilized ovum to the corpus luteum in order that this latter maintains the synthesis of steroid hormones. In order to have a biological action, the hCG must first bind to receptors present in the ovary, essentially at the level of the corpus luteum.

Attempts have already been made to inhibit the function of the hCG in order to provide an immunological method of birth control. For this purpose, vaccines have been suggested which are capable of inducing the formation of anti-hCG antibodies.

In this respect, the patent FR-74 15 780 may be mentioned which describes a vaccine containing as antigen a chemically modified polypeptide and, in particular, chemically modified hCG or $\beta$-hCG.

Mention may also be made of the patent FR 75 23 673 which describes a vaccine containing as antigen a C-terminal fragment of $\beta$-hCG (composed of 30 to 38 amino acid residues). This fragment was chosen in order to avoid cross reactions with related hormones and, in particular, with hLH.

A report of the assays of the anti-hCG vaccines may be found in the article by Vernon Stevens published in Immunology Today (vol. 7, 369, 1986). In particular, this article reports the initial assays carried out using as immunogen the sequence 109–145 of the $\beta$-hCG coupled to diphtheria toxoid. However, the author concluded that it is necessary to develop new anti-hCG vaccines.

It is indeed a fact that the immunogenicity of this vaccine is low and does not give rise to a sufficiently high antibody titer.

In a report in 1985, the World Health Organization (Special program of research development and research training in human reproduction) also concluded that it is necessary to find new immunogens.

Furthermore, it is to be noted that at the third International Congress of Reproduction Immunology, held in Toronto 1–5, Jul. 1986 Aushu Vashishtha et al. referred to the use as immunogen of a peptide conjugated to tetanus toxoid, this peptide consisting of the sequence 21–31 of $\beta$-hCG and sequence 105–115 of $\beta$-hCG-Tyr, these two sequences being linked by a disulfide bridge.

Moreover, an article by Jean Michel Bidart et al. in Molecular Immunology 24, 339, 1987, reports two immunodominant regions in $\beta$-hCG, namely the region 110–116 and the region 134–139.

Is has now been discovered that substantial immunogenic activity is obtained by combining a strongly immunogenic region of $\beta$-hCG, namely the region around the residue 112 of $\beta$-CG and in particular the region 106–116 of $\beta$-hCG, on the one hand, and a sequence of amino acids including a lysine residue, such as those that are found in the sequences which have been highly conserved in the course of the evolution of the $\alpha$ subunits, on the other, and that it is possible in this way to produce a anti-hCG vaccine.

Furthermore, it has also been found that this discovery can be extended to other glycoprotein hormones and in particular to the luteinizing hormones which have an important role in the reproduction of several animal species (cat, dog, etc.).

Consequently, the subject of the present invention is a peptide structure comprising at least.

the sequence 106–116 of a $\beta$-CG or a $\beta$-LH a sequence of at least 5 amino acids containing at least one lysine residue.

The subject of the present invention is more particularly a peptide structure comprising at least.

the sequence 106–116 of $\beta$-hCG a sequence of at least 5 amino acids containing at least one lysine residue.

Another subject of the present invention is a peptide structure comprising at least the sequence 106–116 of a $\beta$-LH a sequence of at least 5 amino acids containing at least one lysine residue.

The sequence 106–116 of $\beta$-hCG is the sequence HPLTCDPRFQ*

\* For the meanings of the symbols for the amino acids see Appendix.

The sequence 106–116 of $\beta$-dLH (canine luteinizing hormone) is the sequence QSIACDRPTLLP (see WO 86/P7383).

The sequence of at least 5 amino acids containing at least one, lysine residue may be in particular a sequence of a $\alpha$-CG containing at least one lysine residue, in particular the sequence 46–55 of $\alpha$-hCG, the sequence 45–49 of $\alpha$-hCG, the sequence 43–55 of $\alpha$-hCG or the sequence 41–58 or 59 of $\alpha$-hCG. However, other sequences are possible provided that they contain at least one lysine residue. In particular, a reverse sequence of a sequence of $\alpha$-hCG containing at least one lysine residue may be involved or even a sequence consisting of any series of amino acids, in addition to a lysine residue.

In the peptide structure according to the invention, the two sequences may be linked together in a linear arrangement, in which case the lysine residue is advantageously separated from the sequence 106–116 of the $\beta$-CG or of the $\beta$-LH by at least 4 amino acids. In this linear arrangement the sequences may be combined in any order, i.e. it is possible to have the arrangement (sequence containing the lysine)—

(sequence 106–116 of β-hCG) or the arrangement (sequence 106–116 of β-hCG)—(sequence containing the lysine).

In addition, the two sequence in the linear arrangement may be separated by an intercalated sequence or "spacer" containing from 1 to 10 amino acids.

The two sequences may also be combined by linkage through an intermolecular or even intramolecular bond. Thus, the two sequences may be linked by a bond between the-COOH group of one of the aspartic acid residues and the free $NH_2$ group of the lysine residue. In the case of an intramolecular bond, the peptide structure has the form of a loop.

In order to enhance the immunogenicity, the peptide structure is advantageously coupled to a carrier by known methods.

Thus, the subject of the invention also includes a synthetic immunogen comprising the peptide structure according to the invention coupled to a carrier.

The carriers may in particular be protein carriers and especially:
1) toxoids:
   tetanus toxoid, fraction II prepared according to the process of Covey et al., Amer. J. Reprod. Immunol. Microbiol. 8, 43 (1985).
   diphtheria and whooping-cough toxoids.
2) anti-diarrhea vaccines (against rotavirus, cholera, Shigellae, *E. Coli* and Salmonellae).
3) the poliomyelitis and yellow fever viruses inactivated by heat and irradiation.
4) membrane proteins of the sporozoite of *P. Falciparus*.
5) KLH (Keyhole Limpet Hemocyanin).

The coupling may be carried out with the aid a coupling agent such as glutaraldehyde, a carbodiimide or bisdiazobenzidine.

Glutaraldehyde leads to coupling between the protein and the lysine residue of the sequence containing at least one lysine residue.

The carbodiimides lead to coupling between the protein and an aspartic acid residue of the sequence 106–116 of a β-CG or a β-LH (for example in the sequence 106–116 of the β-hCG there exist aspartic acid residues in positions 111 and 112).

Coupling with bisdiazo-benzidine requires the presence of a tyrosine residue in the peptide. For this purpose a tyrosine residue is advantageously added to the chain terminus.

The synthetic immunogen can also be prepared according to the MAP (Multiple Antigenic Peptide) technique described by D. Posnett et al (J. Biol. Chem. 263, 17–19, 1988). In this case, the synthetis of the peptide is carried out on a polylysine matrix constructed beforehand. This process gives rise to a "polymer" of the peptide possessing a molecular mass sufficient for it to be immunogenic.

An additional subject of the present invention is an anti-fertility vaccine which comprises a peptide structure according to the invention or preferably a synthetic immunogen according to the invention and a pharmaceutically acceptable vehicle.

In particular, the subject of the present invention is an anti-hCG vaccine which comprises a peptide structure containing at least
the sequence 106–116 of the β-hCG
a sequence of at least 5 amino acids containing at least one lysine residue.
or a synthetic immunogen comprising such a peptide structure coupled to a carrier and a pharmaceutically acceptable vehicle.

In particular, an additional subject of the present invention is an anti-LH vaccine which comprises a peptide structure containing at least
the sequence 106–116 of the β-LH
a sequence of at least 5 amino acids containing at least one lysine residue
or a synthetic immunogen comprising such a peptide structure coupled to a carrier and a pharmaceutically acceptable vehicle.

The synthetic immunogen coupled to its carrier is preferably administered after being mixed with immunization adjuvants. For example, the antigen may be mixed with the N-butyl ester (murabutide) of the muramyl dipeptide (MDP; N-acetyl-glucosamine-3-yl-acetyl-L-alanyl-D-isoglutamine) diluted in a saline solution. The mixture may then be emulsified by means of an equal volume of squalene in the presence of arlacel (excipients). It is also possible to use other adjuvants such as analogues of MDP, bacterial fractions such as streptococcal preparations (OK 432), Biostim (01K2) or modified lipopolysaccharide preparations (LPS), peptidoglycans (N-Opaca) or proteoglycans (K-Pneumonia). In the case of these excipients, water-in-oil emulsions are preferable to oil-in-water emulsions.

The synthetic immunogen can also be administered in the form of biodegradable particles, such as microcapsules or microspheres, preparations of liposomes and nanoparticles. In this case, the immunogen is included in the particle. The purpose of these procedures is to prolong the duration of the action of the vaccine.

The vaccine is administered by the parenteral route (for the vaccines in suspension) and possibly by the oral route (for the vaccines administered in particle form). For example, the emulsion may be injected by the intramuscular route into the triceps muscle. The amount of immunogen used for each injection is variable since it depends on the immune response of each individual. In practice, doses of 50–1000 μg per injection, i.e. 1–20 μg/kg of body weight are used. Several injections are made until a sufficiently high antibody titer is attained; each booster dose is separated from the proceeding one by a period of 4 to 6 weeks. The presence of antibodies directed against the hCG and against a possible carrier protein is checked 5 days after the second booster, then 6 months after the vaccination.

The vaccines according to the invention may also contain other peptides or other immunogens.

Another subject of the present invention is a process for the control of fertility which consists in administering a vaccine according to the invention to a female.

The subject of the present invention is more particularly a process for birth control which consists of administering to a woman a vaccine comprising a peptide structure containing at least.
the sequence 106–116 of the β-hCG
a sequence of at least 5 amino acid containing at least one lysine residue
or a synthetic immunogen comprising such a peptide structure coupled to a carrier and a pharmaceutically acceptable vehicle.

In addition, the peptide structures containing at least:
the sequence 106–116 of the β-hCG
a sequence of at least 5 amino acids containing at least one lysine residue.
can be used to block the hCG receptor and inhibit the development of pregnancy.

Consequently, the subject of the present invention also includes a composition for inducing abortion comprising as active ingredient a peptide structure containing at least.

the sequence 106–116 of the β-hCG
a sequence of at least 5 amino acids containing at least one lysine residue.

The peptide structures according to the invention may be prepared in a standard manner by peptide synthesis on a solid phase or in solution by successive couplings of the different amino acid residues to be incorporated (from the N-terminus toward the C-terminus in solution, or from the C-terminus toward the N-terminus on a solid phase) and the N-termini and the reactive side chains of which are blocked beforehand by appropriate groups which are widely hewn.

Different coupling method my be used:

1. Coupling of the residues by a carbodiimide (for example, N-cyclohexyl-N'-morpholincethylcarbodiimide (CMECDI), dicyclohexylcarbodiimide (DCC), N-ethyl-N'-(3-dimethyl-aminopropyl) carbodiimide (EDC)) with or without a catalyst (example, 1-hydroxybenzotriazole (HOBT) or any other coupling agent (example, N-ethoxy-carbonyl- 2-ethoxy-1,2-dihydroquinoline (EEDQ)).

2. Utilization of the amino acids in the form of preformed symetrical anhydrides.

3. Utilization of the amino acids in the form of active esters (examples, p-nitrophenyl ester, HOBT ester) and coupling through the intermediary of DCC.

However, it is preferable to use the method of synthesis on a solid phase, known as the Merrifield method.

According to this method, a porous polymeric resin is used. Functional groups are grafted onto this resin by different methods. The first amino acid is then attached through its terminal carboxyl function; at the same time, its amino terminal function is protected by a protecting group which is labile. The side chains are also protected and remain so until the end of the synthesis.

After deprotection of the amino terminal function of the amino acid bound to the resin, on the one hand, and activation of the carboxyl function of the amino acid to be coupled, on the other, the formation of the peptide bond is accomplished. After washing and removal of the products of the reaction, another deprotection step is undertaken in order to attach another activated amino acid.

In the last step, after or simultaneously with the removal of the various protecting groups from the side chains, the peptide is cleaved.

In the case in which the protecting group for the amino function is the t-butoxycarbonyl group (t. Boc), it can be removed by treatment of the resin with trifluoroacetic acid.

In such a case, the side chains are protected by groups resistant to the action of trifluoroacetic acid, such as: tosyl for arginine and histidine, benzyl for aspartic acid, benzyloxycarbonyl (Z) for lysine.

When the synthesis of the entire chain has been completed, the protecting groups are removed from the various amino acids, in particular with a solution of a low concentration of hydrogen fluoride in a paracresol/dimethyl sulfide mixture and the peptide is detached from the resin by means of a high concentration of hydrogen fluoride.

The following examples illustrate the present invention:

I—Preparation of the peptide structures

1) Preparation of the peptide (sequence 46–55 of the (α-hCG)—(sequence 106–116 of the β-hCG) (TMLVQKN-VTSHPLTCDDPRFQ).

The synthesis was carried out in an automatic synthesizer Applied Biosystems Model 410A.

The amino function of the amino acids was protected by a t-Boc group and deprotection was carried out by trifluoroacetic acid.

The final deprotection was carried out with a mixture containing 6,5 ml of dimethylsulfide, 1 g of para cresol and 1 ml of HF for 1 g of peptide-resin for 1 h at 0° C. The cleavage of the peptide was carried out at 0° C. with 10 ml of HF and 1 g of para cresol for 1 g of deprotected peptide-resin.

The peptide thus obtained is then purified by exclusion chromatography. It is analyzed after acid hydrolysis by HPLC exchange chromatography and detection with ninhydrin. The sequence is also checked.

The structure of the peptide thus prepared in table I together with those of other peptides prepared in an analogous manner.

TABLE I

| Peptide of the type: sequence with Lys residue - sequence 106–116 β hCG | | |
|---|---|---|
| | Sequence with Lys residue | Sequence 106–116 β-hCG |
| MIMOTOPE 1 with sequence 46–55 α-hCG | TMLVQKNVTS | HPLTCDDPRFQ |
| MIMOTOPE 2 with sequence α inverse | STVNKQVLMT | HPLTC DDPRFQ |
| MIMOTOPE 3 with sequence 45–49 α-hCG | KTLMLV | HPLTCDDPRFQ |
| MIMOTOPE 4 with sequence 43–49 α-hCG | SKKTMLV | HPLTC DDPRFQ |
| MIMOTOPE 5 with sequence 43–55 α-hCG | SKKTMLVQKNVTS | HPLTCDDPFRQ |

2) Preparation of a peptide with a tyrosine residue.

The following peptide is prepared with a view to coupling it through its tyrosine residue to KLH by means of benzidine, This peptide is protected at the C-terminus in the form of —CONH$_2$ TMLVQKNVTSHPLTCDDPRFQYG—CONH$_2$.

3) Preparation of a peptide of the MAP type,

A peptide of the MAP type having the following formula was prepared according to the method described by Posnett et al (reference already cited):

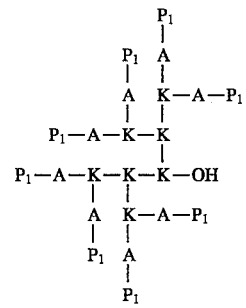

in which P$_1$=TMLVQKNVTSHPLTCDDPRFQ (mimotope 1)

II—Preparation of the synthetic immunogene

1) Coupling to tetanus toxoid

The mimotopic peptide structures were coupled to tetanus toxoid using as coupling agent glutaraldehyde on the one hand and a carbodiimide derivative on the other.

a) Coupling with glutaraldehyde

This coupling agent was chosen in order to give rise to a linkage between the ε-NH$_2$ group of the Lys residue and the ε-NH$_2$ groups of the carrier protein.

The reaction scheme is the following: R1—NH2+OCH—(CH2)3—CHO+NH2—R2→R1—N=CH=(CH2)3—CH=N—R2.

The peptide and the protein are placed in contact in a ratio of 50/1 in 0.1 M bicarbonate buffer containing 0.15 M NaCl, pH=8.5.

Glutaraldehyde (diluted 1/10 in the same buffer) is added dropwise to give a glutaraldehyde/peptide ratio of 50.

The mixture is left for 2 hours at room temperature (yellowing of the solution without precipitation).

An exclusion chromatography is then carried out on a column of Sephadex G25.

Using the peptide structure mimotope 1 a peptide/carrier protein ratio=24 was obtained.

b) Coupling with a water-soluble carbodiimide derivative.

This agent was chosen to establish as principal linkage that between the β-COOH of a residue with a free carboxyl group (aspartic acid: 111 or 112) and the NH$_2$ groups of the carrier protein.

CMECDI was used as the carbodiimide.

Six milligrams of the peptide previously specified are dissolved in 0.5 ml of phosphate/NaCl buffer. 0.2 ml of the solution of CMECDI metho-p-toluene sulfonate (10 mg/ml) are added to this solution. After the peptide coupling agent mixture has been stirred, 5 mg of carrier protein (tetanus toxoid in solution at 6 mg/ml) are added and the mixture is incubated for 2 h at room temperature with stirring. The peptide-carrier protein conjugate is then purified by exclusion chromatography and the conjugate is detected by means of analysis of the proteins according to the Lowry test. The ratio of moles of peptide/moles of carrier protein is determined by means of an amino acid analysis after acid hydrolysis. With mimotope 1, this ratio is 44 moles of peptide per mole of carrier protein.

2) Coupling to KLH

Benzidine (18,8 mg) is dissolved in 1.8 ml of 0.2 M hydrochloric acid by heating gently between 25° C. and 30° C. in order to obtain rapid and complete dissolution, then the solution is cooled and maintained at 0° C.

200 μl of a solution of sodium nitrite containing 14 mg/200 μl and maintained at 0° C. are added dropwise.

The reaction is allowed to proceed for about 3 minutes at 0° C. and then this preparation of bisdiazobenzidine is used immediately.

The following two solutions are mixed at 0° C.:

10 mg of KLH (Keyhole Limpet Hemocyanin; M. W.: 6.5×10$^6$) , i.e. 1.5 mmole in 750 μl of 0.16 M borate buffer, pH 9.1 containing 0.15 M sodium chloride (the insoluble fraction of KLH is removed before the solution is used).

3 mmoles of peptide (i.e. 8mg for the peptide defined under I 1 ) in 750 μl of the same borate buffer, pH 9.1, as used previously.

100 μl of the bisdiazo-benzidine solution are added dropwise.

After a reaction time of only 1 minute, filtration is carried out on Sephadex gel G 25 M (Pharmacia PD10 column: height of 50 mm and diameter of 15 mm) equilibrated beforehand with the 0.15 M sodium chloride also used as eluant.

Fractions of 1 ml are collected. Fractions 3 and 4 (0.6 ml) are stored after a ninhydrin test has been carried out on 10 μl of each fraction. These two pooled fractions contain the peptide coupled to the KLH. A 100 μl aliquot is taken for acid hydrolysis (6N HCl+0.1% phenol) at 110° C. for 18 h. After amino acid analysis, the actual ratio is calculated, i.e. R=1520 in this case, which corresponds to 3.75 mg/ml. (6 mg/1.6 ml).

III—Immunization

At least two rabbits (Fauve de Bourgogne) were immunized with each immunogen.

Immunization protocol 1.1. Preparation of the immunogen for immunization.

The equivalent of 200 μg of peptide (i.e. for the mimotope structure 1 133 μl of peptide/carrier protein solution in the case of the coupling with glutaraldehyde and 167 μl in the case of the coupling with CME-CDI) were diluted in 500 μl of 0.1 M phosphate buffer, pH=7.4, containing 0.15 M NaCl.

Extemporaneous addition of 500 μl of Freund's complete or incomplete adjuvant, depending on the mode of injection, was made to both of these protein solutions.

The mixture was emulsified and then injected.

1.2. Injection timetable D.O. A blood sample was taken (control).

Intradermal injection of the protein solution plus complete Freund's adjuvant (total volume 1 ml).

Ten to twenty points of injection (dorsal region). D.+10 Subcutaneous injection of the protein solution plus incomplete Freund's adjuvant (total volume 1 ml).

A single injection. D.+20 Subcutaneous injection of the protein solution plus incomplete Freund's adjuvant (total volume 1 ml). D.+22 Blood sample taken and presence and titer of antibodies were checked. D.+30 Booster dose identical with that at D.+20. D.+33 Sampling identical with that on D.+22.

1.3. Results of the immunization

The method used to detect the presence and specificity of antibodies directed against the hormones and their subunits is based on a radioimmunological assay(RIA). The hormones (hCG, hLH) and their subunits α-hCG, β-hCG are labeled with a radioactive element (NaI$^{125}$) by using the procedure of Fracker, P. J. and Speck, J. C., Biochem. Biophys. Res. Commun. 80,849 (1978). The antiserum to be tested is incubated with the different labeled molecules (tracers): the antiserum is diluted with an appropriate buffer and a constant amount of tracer is added to each dilution. If antibodies are present in the serum, an antigen (labeled molecule)-antibody complex forms and can be precipitated by polyethylene glycol. The amount of radioactivity precipitated is proportional to the amount of antibody. The specificity of the antibodies is examined in the following manner: to a constant dilution of the antiserum a constant amount of hCG-I$^{125}$ and increasing amounts of the molecules to be tested (hCG, β-hCG, α-hCG, hLH . . . ) are added. The specificity of the antibody is given by the molecule which, at the lowest concentration, brings about a significant displacement of antigen-antibody binding (2 results of the immunization in rabbits).

In the following table are presented the results obtained with the samples of immune sera taken on D22 and which are derived from immunization with immunogens constituted by a peptide structure according to the invention coupled to tetanus toxoid:

TABLE II

|  | Coupling | Number of animals | Number of positive responses | | | |
|---|---|---|---|---|---|---|
|  |  |  | hCG-α | hCG-β | hCG | hLH |
| MIMOTOPE 1 with sequence 46-55 α-hcG | α | 12 | 0 | 11 | 12 | 0 |
|  | β | 18 | 0 | 13 | 14 | 0 |
| MIMOTOPE 2 with sequence | β | 2 | 0 | 0 | 1 | 0 |

TABLE II-continued

| | Coupling | Number of animals | Number of positive responses | | | |
|---|---|---|---|---|---|---|
| | | | hCG- | hCG- | hCG | hLH |
| α inverse MIMOTOPE 4 with sequence 43-49 α-hCG | β | 2 | 2 | 0 | 2 | 1 |
| MIMOTOPE 5 with sequence 43-55 α-hcG | β | 2 | 1 | 2 | 2 | 1 |

α coupling = by means of glutaraldehyde, β coupling by means of carbodiimide.

This table II demonstrates the good results obtained with minotope 1, effective immunization being produced in almost all cases with respect to hCG in the absence of cross reactivity with hLH.

Below are given the results of the mean binding activities to hCG and its subunits of the antisera obtained against minotope 1 (mean+SD)(percentage after dilution 1/10).

| Position of coupling | Number of animals | Binding to: | | |
|---|---|---|---|---|
| | | hCG-α | hCG-β | hCG |
| α | 10 | 0 | 21(12) | 32(17) * |
| β | 10 | 0 | 21(17) | 19(15) ** |

*t = 1.51
**t = 0.18
Significant at p < 0.05 for t > 1.81

The binding activities measured with respect to hCG and its β subunit show that the coupling of the peptide to the α sequence gives higher binding of the antisera obtained with mimotope 1 for hCG.

IV—Biological activity of the antisera

The neutralization of the biological effect of the hCG by a rabbit antibody was determined in the rat by measuring the inhibition of ovulation.

For this purpose, two rats per group were injected with: 1) the pre-immune serum, 2) the immune serum directed against the mimotope 1 obtained in the rabbit, 3)-physiological serum. Eight hours afterwards 500 m IU of hCG were administered. The animals were sacrificed 4 hours later and the appearance (+) or absence (−) of hemorrhagic follicles in each ovary was recorded.

| | Pre-immune serum ovaries | | Antiserum ovaries | | Physiological serum ovaries | |
|---|---|---|---|---|---|---|
| | 1 | 2 | 1 | 2 | 1 | 2 |
| RAT 1 | + | + | − | − | + | + |
| RAT 2 | + | + | − | + | + | + |

These assays demonstrate an antagonistic activity of the antimimotope 1 antisera to the production of ovarian follicles.

| Appendix Symbols for the amino acids | | |
|---|---|---|
| A | Ala | alanine |
| C | Cys | cysteine |
| D | Asp | aspartic acid |
| E | Glu | glumatic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

We claim:

1. A peptide of the sequence:
   Thr Met Leu Val Gln Lys Asn Val Thr Ser bonded to the sequence 106–116 of β-hCG.

2. A peptide as claimed in claim 1 of the sequence:
   Thr Met Leu Val Gln Lys Asn Val Thr Set His Pro Leu Thr Cys Asp Asp Pro Arg Phe Gln.

3. A peptide of the sequence:
   Thr Met Leu Val Gln Lys Asn Val Thr Ser His Pro Leu Thr Cys Asp Asp Pro Arg Phe Gln Tyr Gly-CONH$_2$.

4. A synthetic immunogen comprising a peptide as claimed in claim 1 coupled to a carrier.

5. A synthetic immunogen as claimed in claim 4, wherein the carrier is a protein carrier.

6. A synthetic immunogen as claimed in claim 5, wherein the carrier is tetanus toxoid.

7. A synthetic immunogen as claimed in claim 5, wherein the carrier is Keyhole Limpet Hemocyanin.

8. A synthetic immunogen as claimed in claim 5, wherein the peptide is coupled by means of glutaraldehyde.

9. A synthetic immunogen as claimed in claim 5, wherein the peptide is coupled by a carbodiimide.

10. A synthetic immunogen of the sequence:
    Thr Met Leu Val Gln Lys Asn Val Thr Ser His Pro Leu Thr Cys Asp Asp Pro Arg Phe Gln coupled to a protein carrier.

11. A synthetic immunogen of the sequence:
    Thr Met Leu Val Gln Lys Asn Val Thr Ser His Pro Leu Thr Cys Asp Asp Pro Arg Phe Gln Tyr Gly-CONH$_2$ coupled by a bisdiazo benzidine to a protein carrier.

12. A synthetic immunogen as claimed in claim 4, wherein the peptide is coupled to a polylysine matrix.

* * * * *